(12) United States Patent
Campbell

(10) Patent No.: US 6,805,682 B1
(45) Date of Patent: Oct. 19, 2004

(54) FLUID APPLICATOR

(76) Inventor: Mark C. Campbell, 1887 E. Packard Dr., Saginaw, MI (US) 48603

( * ) Notice: Subject to any disclaimer, the term of this patent is extended or adjusted under 35 U.S.C. 154(b) by 86 days.

(21) Appl. No.: 10/138,057

(22) Filed: May 3, 2002

(51) Int. Cl.[7] .......................... A61M 35/00; B43K 5/06; B05C 21/00
(52) U.S. Cl. ............................ 604/1; 401/176; 401/196
(58) Field of Search .................. 604/1–3; 401/146, 401/143, 150, 176, 178, 179, 196, 197, 207

(56) References Cited

U.S. PATENT DOCUMENTS

| | | | |
|---|---|---|---|
| 2,679,064 A | | 5/1954 | Palma, Jr. et al. |
| 2,995,768 A | | 8/1961 | Skuratowicz |
| 4,169,547 A | * | 10/1979 | Newell ........................ 222/386 |
| 4,415,288 A | | 11/1983 | Gordon |
| 4,732,503 A | | 3/1988 | Bader et al. |
| 5,088,849 A | * | 2/1992 | Johnson et al. ............... 401/44 |
| 5,167,069 A | | 12/1992 | Quinn |
| 5,573,342 A | | 11/1996 | Patalano |
| D381,460 S | | 7/1997 | Libbey |
| D392,411 S | | 3/1998 | Mayo |
| 5,851,077 A | | 12/1998 | Trejo |
| 5,934,296 A | | 8/1999 | Clay |
| 6,010,268 A | | 1/2000 | Sereg et al. |
| 6,042,286 A | | 3/2000 | Pazienza |
| 6,045,279 A | | 4/2000 | Follis |
| 6,079,075 A | | 6/2000 | Velez-Juan |
| 6,126,352 A | | 10/2000 | Wiley |
| 6,200,055 B1 | * | 3/2001 | Fusaro, Jr. .................. 401/178 |
| 6,245,037 B1 | * | 6/2001 | Reum et al. ................... 604/1 |
| 6,536,975 B1 | * | 3/2003 | Tufts .......................... 401/134 |

* cited by examiner

Primary Examiner—John J. Calvert
Assistant Examiner—Linh Truong
(74) Attorney, Agent, or Firm—John K. McCulloch

(57) ABSTRACT

A fluid applicator has a fluid-containing cask within which is a displaceable piston operable in response to operation of a piston controller to dispense fluid through a dispensing valve from the cask to an applicator. A handle is removably coupled to the cask to facilitate the application of fluid to a selected site. The handle may be separated from the cask without impairing the ability of the piston to displace fluid from the cask. The valve is manually adjustable to enable a selected quantity of fluid to be dispensed cask.

24 Claims, 5 Drawing Sheets

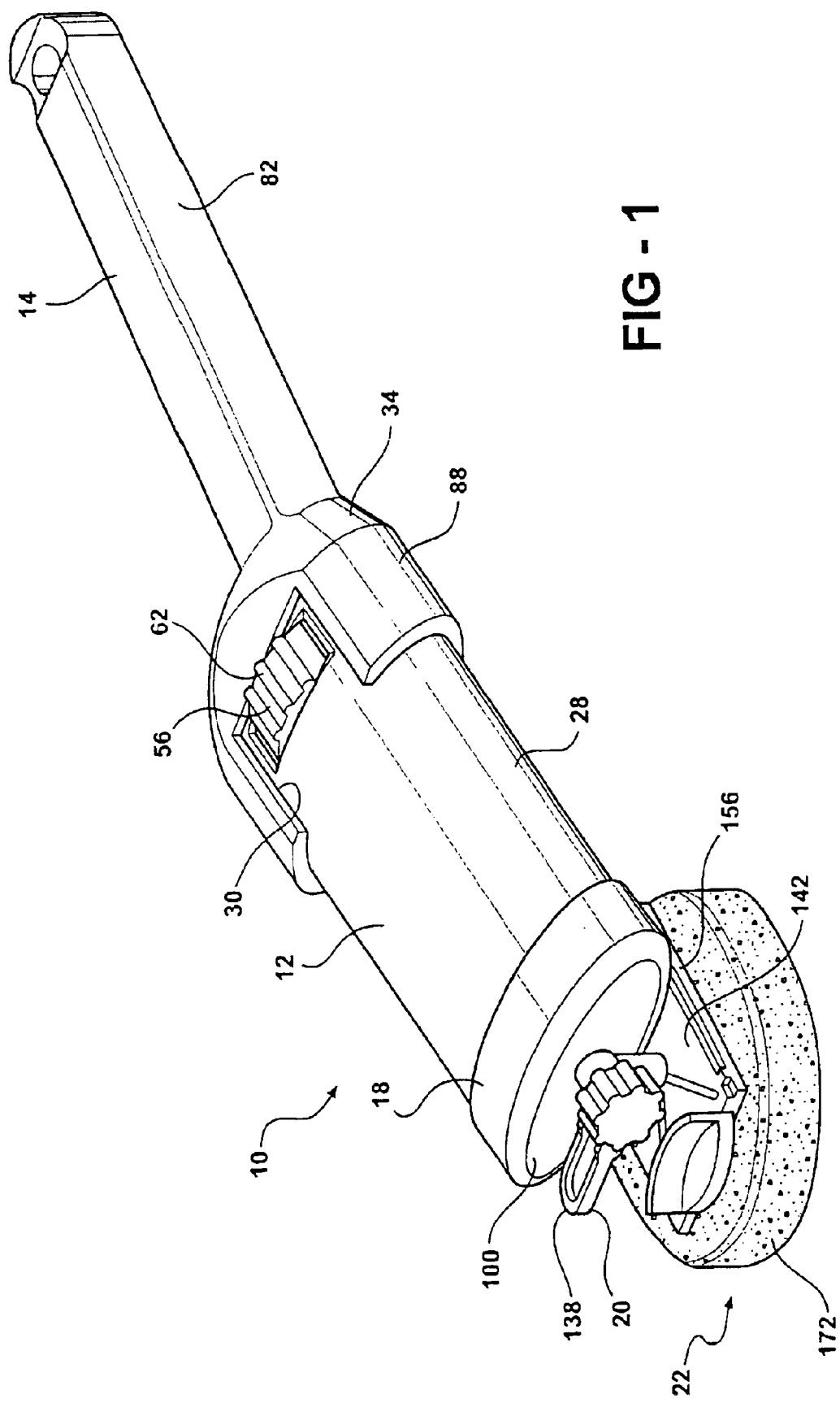

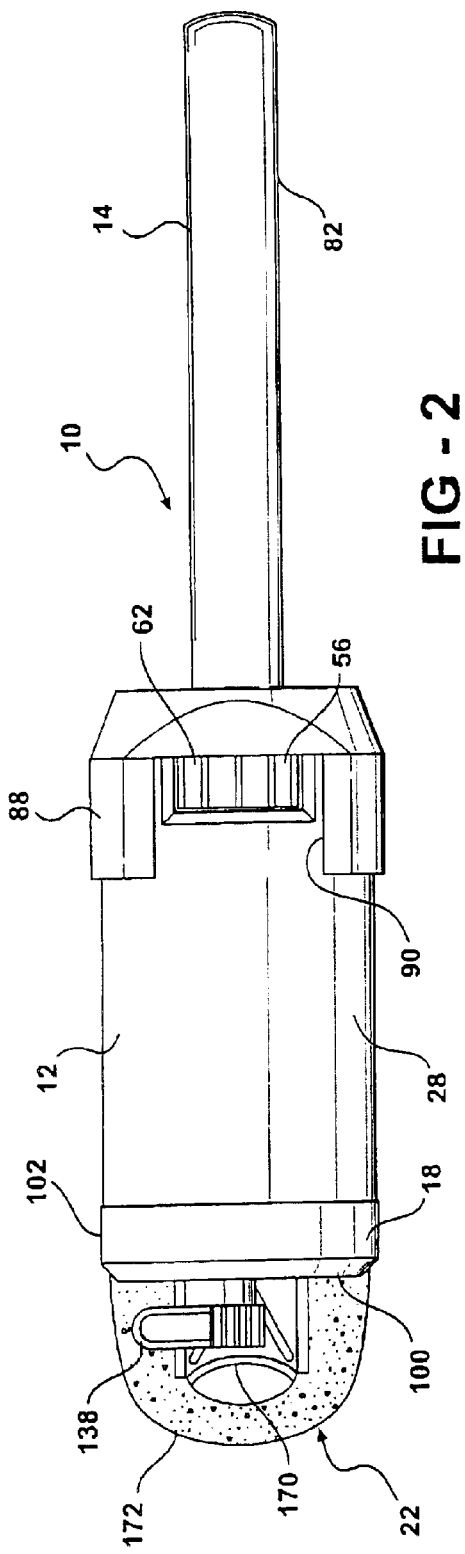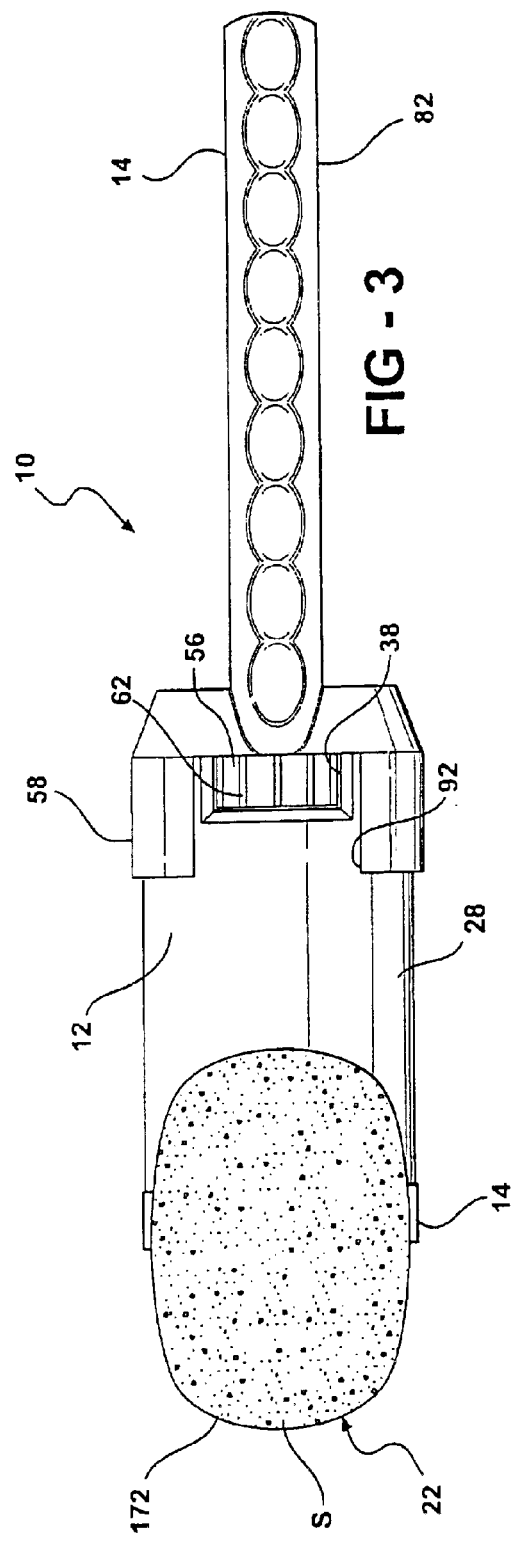

FLUID APPLICATOR

TECHNICAL FIELD

The fluid applicator has a refillable cask and applies various fluids with different viscosities to skin to treat skin conditions, block sun rays, repel insects, apply ointments, or apply cleansing agents.

BACKGROUND OF THE INVENTION

Personal applicators have been used to dispense fluids such as medicated lotions, ointments, sun screen lotions and sun block lotions. Many of these fluids have a viscosity at normal room temperatures that is similar to the viscosity of water at the same temperature. A discharge valve is generally provided to control the flow of such fluids that run easily to an applicator. Fluid dispensers with discharge valves that control the flow of fluid to an applicator generally do not have a pump to force fluid into the applicator. When the fluid flows freely and the container can be inverted, a pump is not required. A discharge valve is generally provided to prevent the supply of excess freely flowing fluid to an applicator.

Fluid dispensers and fluid applicators for fluids that flow slowly or do not flow at normal room temperatures require a pump to force a fluid out of the fluid reservoir. Pistons that are advanced by a manually rotated screw have been used to force a fluid to the applicator. Other fluid dispensers have employed spring loaded pistons to force fluid from a reservoir. A discharge pump is employed in combination with some spring loaded pistons to control the rate of discharge and to increase the pressure of the discharged fluids.

Known fluid applicators are often designed to dispense one specific fluid. As a result these applicators are not capable of dispensing a fluid with a substantially different viscosity than the fluid they were designed to dispense. Some of the known fluid dispensers are filled with a fluid prior to purchase and are not intended to be refilled.

SUMMARY OF THE INVENTION

The fluid applicator, for applying fluids to skin, includes a tubular cask with an open handle end, an open dispensing end, and a cask inside surface. A fluid metering assembly includes a piston slideably mounted in the tubular cask and in sealing and sliding engagement with the cask inside surface. A piston controller connected to the piston and the cask is operable to advance the piston toward the open dispensing end of the cask. A discharge end cap is removably connected to the open dispensing end of the tubular cask. The discharge end cap includes a valve chamber, an applicator platform, and a fluid flow passage having a passage inlet in communication with the valve chamber. The fluid flow passage extends through the applicator platform. A valve is mounted in the valve chamber and is movable between an open position and a closed position. A fluid distribution pad is mounted on the applicator platform and is in communication with a discharge end of the fluid flow passage.

The piston controller includes an elongated screw, in engagement with a threaded bore in the piston, and a knob integral with the elongated screw. The knob is rotatable relative to the cask. The knob is also radially and axially fixed relative to the cask. A handle telescopically receives the handle end of the cask. The fluid applicator can be used with or without the handle.

BRIEF DESCRIPTION OF THE DRAWINGS

The presently preferred embodiment of the invention is disclosed in the following description and in the accompanying drawings, wherein:

FIG. 1 is a perspective view of the fluid applicator;

FIG. 2 is a reduced top plan view of the fluid applicator;

FIG. 3 is a bottom plan view of the fluid applicator;

DESCRIPTION OF THE PREFERRED EMBODIMENT

Figure 4:
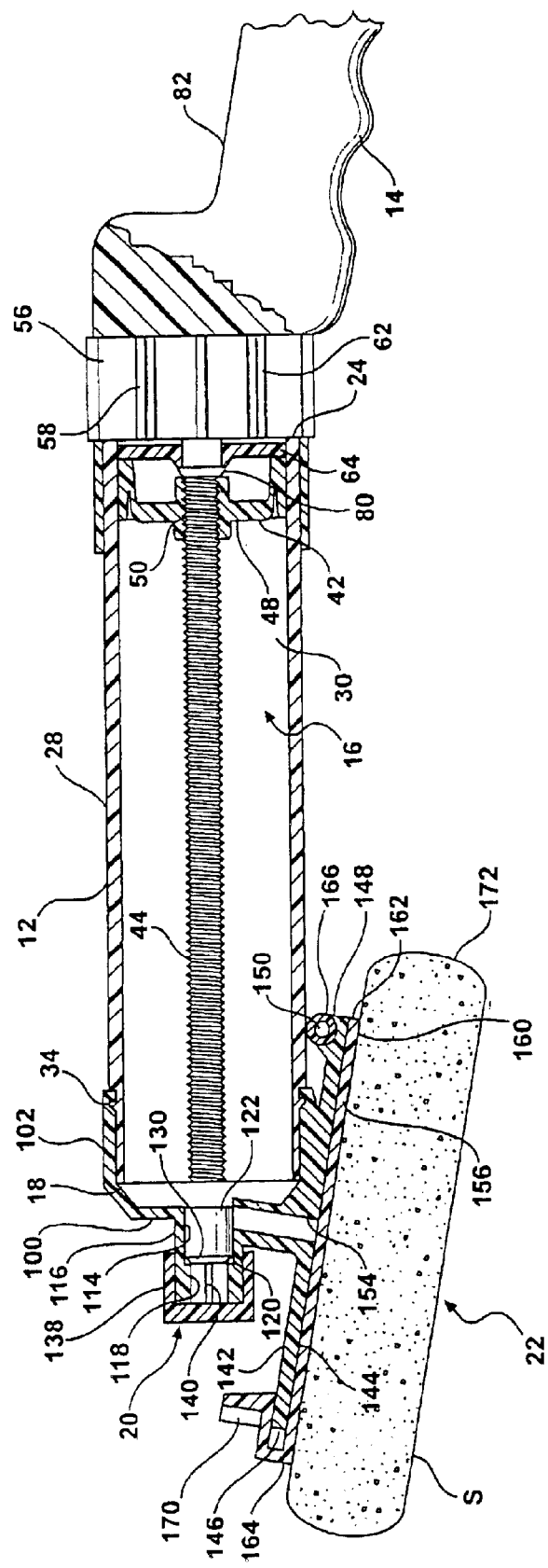
FIG. 4 is an enlarged side elevational view with parts broken away.
Figure 5:
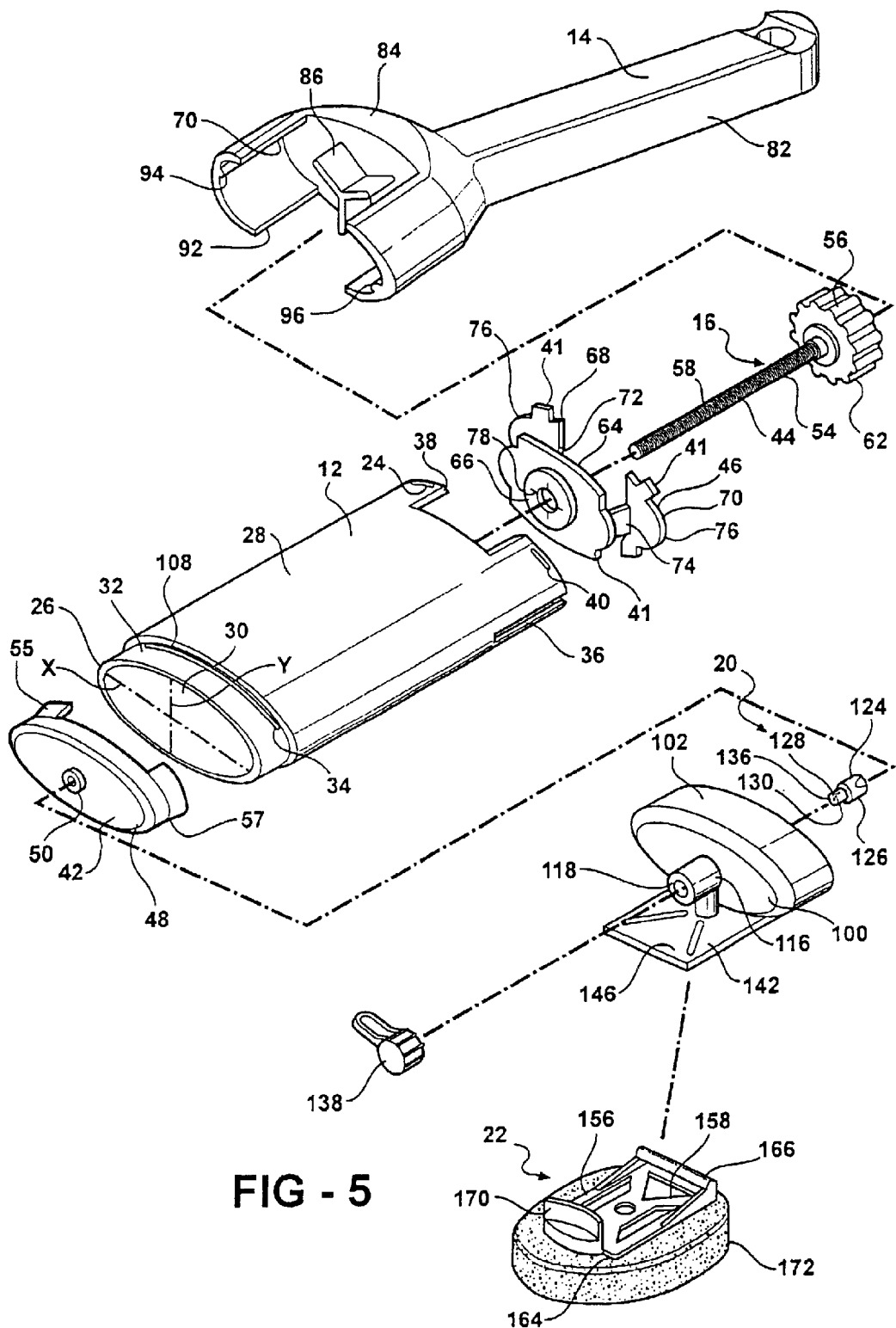
FIG. 5 is an expanded perspective view of the lotion applicator.
Figure 6:
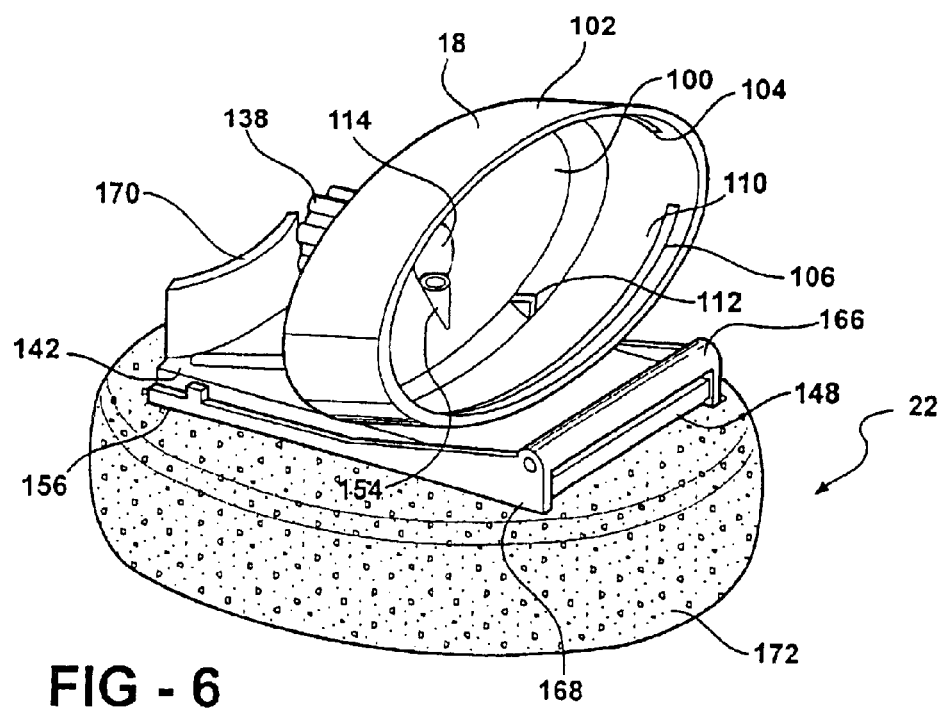
FIG. 6 is an enlarged perspective view of the discharge end cap assembly and applicator assembly.
Figure 7:
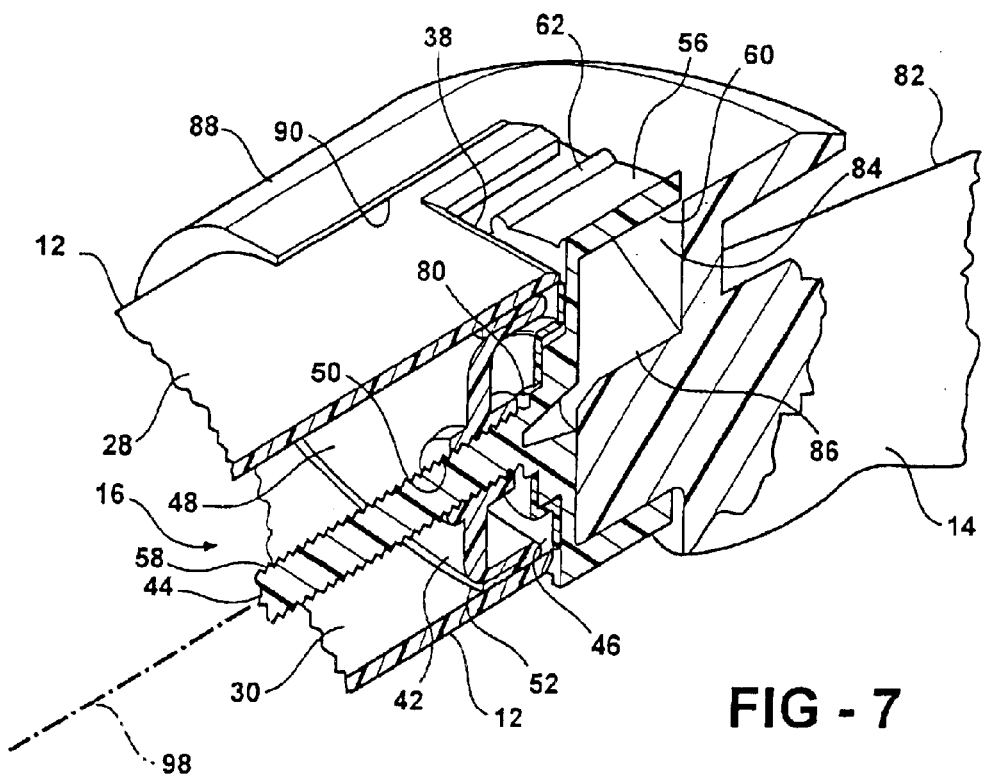
FIG. 7 is a perspective sectional view of the handle assembly, the fluid metering and dispensing assembly with parts broken away.

The fluid applicator 10 has a tubular cask 12, a handle assembly 14, a fluid metering and dispensing assembly 16, a discharge end cap assembly 18, a discharge valve assembly 20, and an applicator assembly 22. The tubular cask has an elliptical cross-sectional shape as shown in drawing FIG. 5. The cross-sectional shape can be varied somewhat if desired. However, the inside cross-sectional shape and size is uniform from one end to the other of the cask 12. The cask 12 has an open handle end 24, an open dispensing end 26, an outside surface 28, and a smooth interior surface 30. A discharge end cap sealing surface 32 is provided on the outside of the cask 12 adjacent to the dispensing end 26. Discharge end cap retainer flanges 34 are provided on the end cap sealing surface 32. These retainer flanges 34 cannot extend into the portion of the end cap sealing surface 32 adjacent to a long axis X of the elliptical cross-sectional shape of the cask 12. The open handle end 24 of the cask 12 has two handle alignment grooves 36 in the outside surface 28 that are parallel to a central axis of the cask, and the long axis X of the elliptical cross-sectional shape passes through both handle alignment grooves. Two piston controller knob notches 38 are provided in the cask 12 adjacent to the open handle end 24. These notches 38 pass completely through the cask walls and are centered on the short axis Y of the elliptical cross-sectional shape. Controller retainer slots 40 also pass through the cask 12.

The fluid metering and dispensing assembly 16 includes a piston 42, a piston controller 44 and a controller retainer 46. The piston 42 has a transverse plate 48 with a central threaded bore 50. A flexible piston seal 52 is integral with the plate 48, surrounds the plate 48, and is in sealing contact with the interior surface 30 of the tubular cask 12. Piston guide skirts 55 and 57 extend axially toward the open handle end 24 of the cask 12 from outboard ends of the transverse plate 48.

The piston controller 44 includes an elongated shaft 54 with an integral rotatable knob 56 on one end. The elongated shaft 54 has a lead screw 58 extending substantially its entire length. The rotatable knob 56 has a cylindrical bore 60 in its end opposite the shaft 54. A plurality of metering bars 62 extend radially outward from the knob 56.

The controller retainer 46 has a central retainer plate 64 with a central bore 66. Two retainer wing plates 68 and 70 are connected to the central retainer plate 64 by post members 72 and 74. These post members 72 and 74 are generally parallel to the piston controller 44. The wing plates 68 and 70 both have elliptical outer surfaces 76. Controller retailer tabs 41, that extend outward from the surface 76 on the wing plates 68 and 70, are inserted into controller retainer slots 40 to axially position the controller retainer 46. Slots 78 extend radially outward from the central bore 66 a short distance.

The elongated shaft 54 of the piston controller 44 extends through the central bore 66 of the retainer 46. The slots 78 permit a circular flange 80 on the shaft 54 to be forced through the central bore 66. In this position the controller retainer 46 is axially fixed relative to the piston controller 44. The lead screw 58 of the piston controller 44 is screwed into the threaded bore 50 through the piston 42. The piston 42 is gently pressed into the handle end 24 of the cask 12. The post members 72 and 74 and the central retainer plate 64 provides sufficient flexibility to move the tabs 41 projecting outward from the elliptical outer surfaces 76 into the controller retainer slots 40 through the cask 12. The controller retainer 46 is axially fixed when the tabs 41 on the retainer wing plates 68 and 70 are seated in the controller retaining slots 40 in the cask 12.

The handle assembly 14 includes an elongated handle 82 with an integral cask holder base plate 84. Three blade members 86 extend outward from the opposite side of the base plate 84 from the handle 82. The three blade members 86 cooperate to form a rotatable knob support trunnion that supports the rotatable knob 56 and limits radial movement of the knob. A skirt 88 is integral with the base plate 84 and surrounds the base plate with the exception of two rectangular skirt notches 90 and 92. The skirt notches 90 and 92 are centered on the minor axis Y of the elliptical skirt 88, and expose the rotatable knob 56 and may be larger than the piston control knob notches 38. The portions of the skirt 88 on each side of the skirt notch 90 and 92 telescopically receive the open handle end 24 of the tubular cask 12. The inside surfaces of the two skirt portions 88 have the same elliptical shape as the ends of the elliptical tubular cask 12 that are centered on the long axis X of the ellipse. During attachment of the handle assembly 14 to the cask 12, guide flanges 94 and 96, shown in FIG. 5, on the skirt sections 88 slide into handle alignment grooves 36 in the cask. The guide flanges 94 and 96 have a slight taper so that they wedge against the sides of the slots 36, when the handle end 24 of the cask 12 contacts the base plate 84. Friction holds the cask 12 on the handle 14. However, tabs that snap into grooves can be added, to retain the handle assembly 14 on the cask 12, if needed. When the handle 14 is attached to the cask 12, a long axis of the elongated handle 82 intersects a long axis 98 of the cask 12 at an angle between 10° and 15°.

The discharge end cap assembly 18 includes a discharge end plate 100. A cask retainer skirt 102 that encircles the plate 100 and is shaped to telescopically receive the opened dispensing end 26 of the cask 12. Discharge end cap grooves 104 and 106 in the inside of the cask retainer skirt 102 receive the discharge end cap retainer flanges 34 and releasably retain the cask 12 in the skirt. Sealing surfaces 108 on the discharge end of the cask 12 contact the inside skirt surface 110 of the cask retainer skirt 102 to form a liquid tight seal. Stops 112 limit movement of the cask 12 into the discharge end cap 18. Pressure is applied to the ends of the skirt 102 to force the skirt ends toward each other and release the grooves 104 and 106 from the flanges 34 when removing the end cap assembly 18 from the cask 12.

A discharge valve chamber 114 is formed in the discharge end plate 100. A cylindrical boss 116, that is integral with the end plate 100 extends from the end plate 100 on the opposite side from the retainer skirt 102. The valve chamber 114 is cylindrical. A valve shank bore 118 extends from the valve chamber 114 and through the cylindrical boss 116. The bore 118 has a smaller diameter than the valve chamber 114. A seal surface 120 is formed at the junction between the chamber 114 and the bore 118.

A rotatable cylindrical valve 122 is inserted into the valve chamber 114 from the side of the end plate 100 with the cask retainer skirt 102. The large diameter portion 124 of the valve 122 is a cup shaped member with a fluid passage 126 through its wall. A valve shank 128 is integral with the cup bottom and co-axial with the large diameter portion 124. A sealing surface 130 on the valve 122 cooperates with the seal surface 120 on the end wall of the valve chamber 114 to prevent leakage through the shank bore 118 and the boss 116. A seal can be created by direct contact between the sealing surfaces 120 and 130 or a seal member such as an O-ring can be mounted between the two sealing surfaces. The valve shank 128 is journaled in the shank bore 118. At least one shank slot 136 in the valve shank 128 is parallel to the axis of the valve. A valve actuator lever 138 is journaled on the cylindrical boss 116 and has an integral blade 140 that is received in the slot 136 so that rotation of the actuator lever rotates the valve 122. A tit on one member is received in a recess (not shown) on the other member to lock the lever 138 to the shank 128.

An applicator platform 142 is integral with the end plate 100 of the discharge end cap assembly 18. The applicator platform 142 has a flat bottom surface 144 that faces away from the end plate 100, an applicator latch engaging surface 146 and a second end 148 with a cradle 150. The cradle 150 faces away from the bottom surface 144 and the applicator latch engaging end 146. A fluid flow passage 154 extends from the discharge valve chamber 114 and through the applicator platform 142.

The applicator assembly 22 includes an applicator deck or frame 156 with a flat top surface 158, a bottom surface 160, a pivot end 162 and a latch end 164. A pivot bar 166 has its ends secured to end plates 168 on the deck 156. The pivot bar 166 is above the pivot end 162 and spaced from the top surface 158 of the deck 156. A latch 170 is integral with the latch end 164 of the deck 156. An applicator fluid distributor pad 172 is secured to the bottom surface 160 of the deck 156. Various pads 172 can be used. A sponge block or fiber pad would generally be acceptable for an applicator fluid distributor pad 172. A swab would also be acceptable for a pad 172. An adhesive can be used to secure a pad 172 to the deck bottom surface 160. However, other systems could be used to secure an applicator pad 172. The density of the applicator pad 172 can be selected to apply a given fluid at a desired rate. Passages can also be formed in the applicator pad 172 to further control the flow of fluid into and through an applicator pad. Some applicator pads 172 can be cleaned as required. Disposable applicator pads 172 may also be used.

The applicator assembly 22 is attached to the applicator platform 142 by first placing the pivot bar 166 on the cradle 150. After the pivot bar 166 is seated on the cradle 150, the deck 156 is pivoted about the axis of the pivot bar and toward the applicator platform 142. As the deck 156 approaches the bottom surface 144 of the applicator platform 142, the latch 170 is cammed away from the pivot bar 166 and moved across the latch end 146 of the applicator platform. The latch 170 then springs back toward the pivot bar 166, engages a latch engaging surface 146 on the applicator platform 142 and latches the applicator assembly 22 to the applicator platform. The applicator deck 156 is preferably made from a resilient plastic material which permits the latch 170 to be unlatched and relatched.

The applicator assembly 22 including the deck 156 and fluid distributor pad 172 can be changed as a unit. It is also possible to change the pad 172 used on the deck 156 if the connection between the deck and the pad permits separation of the pad.

The applicator platform 142 has a flat bottom surface 144 that is in a plane that intersects the long axis of the cask 12 and the coaxial axis of the elongated shaft 54 of the piston controller 44 at an angle between 10° and 15°. This places the skin contact surface S of the pad 172, which is parallel to the bottom surface 144, in a plane that is generally parallel to the long axis of the elongated handle 82. This arrangement moves the open handle end 24 of the cask 12 away from a surface to which fluid is being applied. The distance the open handle end 24 of the cask 12 is moved from the plane of the skin contact surface S is sufficient to permit the pad 172 to be generally parallel to the skin that is being treated. Positioning the long axis of the elongated handle 82 parallel to the skin contact surface S makes it easier to control contact between the pad 172 and skin areas.

To prepare the fluid applicator for use, the piston 42 is retracted toward the handle assembly 14 and the discharge end cap 18 is removed from the cask 12 by applying force manually to move the discharge end cap away from the cask. The cask 12 is then filled with the fluid that is to be applied. The discharge end cap 18 is then forced back into sealing contact with sealing surface 32 on the discharge end 26 of the cask 12. Some air may need to be removed from the cask 12. The rotatable valve 122 is rotated to a closed position by rotating the valve actuator lever 138. An applicator assembly 22 with an appropriate applicator fluid distributor pad 172 for the fluid filling the cask 12 is attached to the applicator platform 142 as explained above. The fluid applicator 10 is then placed in the storage area until the fluid is needed.

To use the fluid applicator 10, the rotatable valve 122 is rotated to an open position by moving the valve actuator lever 138 to an open position. The knob 56 is then rotated to advance the piston 42 and supply the desired quantity of fluid to the applicator assembly 22. If the quantity of fluid applied to the applicator assembly is to be metered, the number of metering bars 62, passing through one of the piston control knob notches 38, 90 or 92 are counted. A clicker that makes an audible sound upon the passage of each metering bar 62 can be added if desired. The metering bars 62 can also be numbered to assist in measuring movement of the piston 42. The fluid distributor pad 172 is then rubbed on the area of the skin to be treated. If the fluid being applied flows easily, the valve 122 is rotated to a closed position before the applicator pad 172 is rubbed on the skin area to ensure that there is no leakage. Additional fluid is supplied to the applicator pad 172, as required, by opening the valve 122 and rotating the knob 56 to advance the piston 42 and pump additional fluid into the applicator.

The controller retainer 46 positions the retainer and rotatable knob 56 and the elongated shaft 54 with the lead screw 58. Employment of the controller retainer 46 makes it possible to use the fluid applicator 10 either with the handle assembly 14 or without the handle assembly. When the handle assembly 14 is removed, the cask 12 can sit on the handle end 24 in a vertical position for refilling the cask. The controller retainer 46 also makes it possible to remove the handle assembly 14 to reduce the total length of the fluid applicator 10 for storage and for packing in a suitcase for travel. The fluid applicator 10 can be used without the controller retainer 46 when the features described above are not required. During employment of the application 10 without the controller retainer 46, the rotatable knob 56 is radially fixed by blade members 86 and is axially retained by the control knob notches 38 in the cask 12 and by the cask holder base plate 84 of the handle assembly 14.

The cask 12 can be made from an acrylic resin or other suitable material. The other parts can be made from polypropylene or other suitable materials.

The disclosed embodiment is representative of a presently preferred form of the invention, but is intended to be illustrative rather than definitive thereof. The invention is defined in the claims.

I claim:

1. A fluid applicator, for applying fluids to a selected site, comprising:

a tubular cask including a handle end and a dispensing end, said cask having a non-circular inside surface;

a fluid metering assembly including a piston slideably mounted in said tubular cask and in sealing and sliding engagement with the cask inside surface, and a piston controller connected to the piston and the cask and operable to advance the piston toward the dispensing end of the cask, said piston having a non-circular configuration corresponding substantially to that of the inside surface of said cask;

a discharge end cap removably connected to the dispensing end of said tubular cask and including a valve chamber, an applicator platform, and a fluid flow passage having a passage inlet in communication with the valve chamber and wherein the fluid flow passage extends through the applicator platform;

a manually accessible adjustable valve mounted in the valve chamber and movable between a closed position and a selected one of a plurality of open portions; and a fluid distributor pad mounted on the applicator platform and in communication with a discharge end of the fluid flow passage.

2. A fluid applicator for applying fluids to a selected sites comprising:

a tubular cask including a handle end and a dispensing end, said cask having a non-circular inside surface;

a fluid metering assembly including a piston slideably mounted in said tubular cask and in sealing and sliding engagement with the cask inside surface, and a piston controller connected to the piston and the cask and operable to advance the piston toward the dispensing end of the cask, said piston having a non-circular configuration corresponding substantially to that of the inside surface of said cask;

a discharge end cap removably connected to the dispensing end of said tubular cask and including a valve chamber, an applicator platform, and a fluid flow passage having a passage inlet in communication with the valve chamber and wherein the fluid flow passage extends through the applicator platform;

a manually accessible adjustable valve mounted in the valve chamber for movements between open and closed positions; and a fluid distributor pad mounted on the applicator platform and in communication with a discharge end of the fluid flow passage.

3. A fluid applicator, as set forth in claim 2, wherein the piston controller includes an elongated screw that screws into a threaded bore in the piston, a rotatable knob integral with an end of the elongated screw, and a retainer plate assembly that axially positions the rotatable knob.

4. A fluid applicator, as set forth in claim 3, wherein the retainer plate assembly includes a central retainer plate with a bore that receives the elongated screw, a plurality of retainer wing plates connected to the central retainer plate, and wherein a projection on a radially outer surface of each of the plurality of wing plates is received in a controller recess in the smooth interior surface of the cask to axially fix the retainer plate assembly.

5. A fluid applicator, as set forth in claim 4, wherein each of the plurality of retainer wing plates is connected to the central retainer plate by at least one post member.

6. A fluid applicator, as set forth in claim 2, wherein said tubular cask inside surface has an elliptical cross-section.

7. A fluid applicator, as set forth in claim 2, including a handle assembly that telescopically and removably is coupled to the handle end of said tubular casks.

8. A fluid applicator, as set forth in claim 2, including a handle assembly removably attached to the handle end of said tubular cask and wherein the piston controller includes an elongated screw that screws into a threaded bore in the piston and has a control knob fixed on the handle assembly.

9. A fluid applicator, as set forth in claim 2, wherein the valve mounted in the valve chamber includes a cylindrical portion with a fluid passage, a valve shank integral with the cylindrical portion and extending into a valve shank bore in the discharge end cap, and a valve actuator connected to the valve shank.

10. A fluid applicator, as set forth in claim 9, including a fluid seal between the cylindrical portion of the valve and a valve chamber seal surface extending between a cylindrical valve chamber wall and the valve shank bore.

11. A fluid applicator, as set forth in claim 2, wherein the applicator assembly includes an applicator deck that is releasably secured to the applicator platform, and the fluid distributor pad is connected to the applicator deck.

12. A fluid applicator, as set forth in claim 11, wherein the fluid distributor pad includes a sponge.

13. A fluid applicator, as set forth in claim 11, wherein the fluid distributor pad includes a swab.

14. A fluid applicator, as set forth in claim 2, wherein the piston includes a flexible piston seal and at least one piston guide skirt.

15. A fluid applicator, as set forth in claim 2, wherein the piston includes two piston guide skirts that engage the cask inside surface.

16. A fluid applicator, for applying fluids to skin, comprising:
- a tubular cask with an open handle end, an open dispensing end, and a cask inside surface;
- a fluid metering assembly including a piston slideably received in said cask and having an integral flexible seal on a piston periphery that is in sealing contact with the cask inside surface around the entire circumference of the piston, and a piston controller connected to the piston and said cask and operable to advance the piston toward the open dispensing end of said cask;
- a discharge end cap including a discharge end plate, a cask retainer skirt surrounding the discharge end plate and in sealing engagement with said cask, a valve chamber in the discharge end plate, and a valve passage in the discharge end plate that joins the valve chamber;
- a manually accessible adjustable valve mounted in the valve chamber, a valve actuator connected to the valve and operable to move the valve between an open position and a closed position, a valve fluid passage in the valve, and a valve seal surface on the valve that cooperates with a valve chamber seal surface to prevent fluid leakage through the valve fluid passage
- an applicator platform connected to the discharge end cap and including an end cap fluid flow passage in communication with the valve chamber and extending through the applicator platform; and
- a fluid distributor pad attached to the applicator platform in a position to receive fluid from said cask when the valve is in the open position and the valve fluid passage connects the end cap fluid flow passage to said tubular cask.

17. A fluid applicator, as set forth in claim 16, wherein the fluid distributor pad attached to the applicator platform includes an applicator deck releasably connected to the applicator platform and a sponge secured to the applicator deck.

18. A fluid applicator, as set forth in claim 16, wherein the fluid distributor pad attached to the applicator platform includes an applicator deck releasably connected to the applicator platform and a swab secured to the applicator deck.

19. A fluid applicator, as set forth in claim 16, including a handle connected to the open handle end of said tubular cask.

20. A fluid applicator, as set forth in claim 16, wherein the fluid distributor pad has a skin contact surface that is substantially in a skin contact plane that intersects a cask center line at an angle between nine degrees and sixteen degrees.

21. A fluid applicator, as set forth in claim 20, including a handle connected to the open handle end of said tubular cask and having a handle axis that is substantially parallel to the skin contact plane.

22. An applicator, for applying fluids to skin, comprising:
- a tubular cask with an open handle end, an open dispensing end, and a cask non-cylindrical inside surface;
- a fluid metering assembly including a piston slideably mounted in said tubular cask, and having a non-cylindrical piston seal in sealing contact with the cask non-cylindrical inside surface, an elongated shaft with integral knob on one end and a lead screw in engagement with a threaded piston bore through the piston, a central retainer plate supported by the open handle end of said tubular cask and limiting axial movement of the integral knob toward the open dispensing end, a cask holder base plate attached to the open handle end of said tubular cask, rotatably supporting the integral knob, and limiting movement of the integral knob and the elongated shaft away from the dispensing end;
- a discharge end cap closing the discharge end of said tubular cask;
- an applicator platform connected to the discharge end cap;
- an applicator assembly connected to the applicator platform; and
- a discharge valve connected to the discharge end cap that is shiftable between a closed position and an open position in which a fluid flow path through the discharge valve and a fluid flow passage are open to transmit fluid from said tubular cask to the applicator assembly.

23. An applicator, as set forth in claim 22, including a handle integral with the cask holder base plate.

24. A method of assembling a fluid applicator for use comprising:
- inserting a piston with a non-cylindrical peripheral seal into a tubular cask with the non-cylindrical peripheral seal in sealing engagement with a cask inside surface;
- screwing an elongated shaft, with a lead screw and an integral rotatable knob, into a threaded bore through the piston;
- axially anchoring the elongated shaft relative to said tubular cask;
- inserting a cylindrical valve into a valve chamber in a discharge end cap and a valve shank integral with the cylindrical valve into a valve shank bore;
- mounting a valve actuator on the discharge end cap for pivotal movement relative to the discharge end cap and connecting the valve actuator to the valve shank,
- holding a sealing surface on the cylindrical valve in sealing engagement with a valve chamber end wall;

attaching an applicator deck with a fluid distributor pad to the discharge end cap in a position to receive fluid from said cylindrical cask; and forcing a discharge end of said cylindrical cask into a cask retainer skirt on the discharge end cap until the discharge end cap retainer flange snaps into a discharge end cap groove and a fluid seal is formed between the discharge end cap and said cylindrical cask.

* * * * *